United States Patent
Brunk et al.

(10) Patent No.: US 11,947,060 B2
(45) Date of Patent: Apr. 2, 2024

(54) DEVICE FOR VALIDATING THE AXIS LINEARITY AND/OR THE POSITIONING ACCURACY OF A DISPLACEMENT MECHANISM FOR A RADIATION DETECTOR AND ASSOCIATED METHOD OF PRACTICE

(71) Applicant: LAP GmbH Laser Applikationen, Lüneburg (DE)

(72) Inventors: Markus Brunk, Neetze (DE); Daniel Bojara, Deutsch Evern (DE)

(73) Assignee: LAP GmbH Laser Applikationen

(*) Notice: Subject to any disclaimer, the term of this patent is extended or adjusted under 35 U.S.C. 154(b) by 92 days.

(21) Appl. No.: 17/737,246

(22) Filed: May 5, 2022

(65) Prior Publication Data
US 2022/0357473 A1 Nov. 10, 2022

(30) Foreign Application Priority Data
May 6, 2021 (DE) .................. 10 2021 111 815.8

(51) Int. Cl.
*G01T 7/00* (2006.01)
*G01B 21/24* (2006.01)

(52) U.S. Cl.
CPC .............. *G01T 7/005* (2013.01); *G01B 21/24* (2013.01)

(58) Field of Classification Search
CPC ....... A61N 5/1075; G01T 7/005; G01B 21/24
See application file for complete search history.

(56) References Cited

U.S. PATENT DOCUMENTS

| 5,313,410 | A | 5/1994 | Watts |
| 9,149,657 | B2 | 10/2015 | Schule |
| 2018/0117361 | A1* | 5/2018 | Pencea ...................... G01T 1/29 |
| 2020/0101327 | A1 | 4/2020 | Alquist et al. |

FOREIGN PATENT DOCUMENTS

| CN | 102473471 A | 5/2012 |
| DE | 29822001 U1 | 3/1999 |
| DE | 102010054995 B3 | 3/2012 |
| DE | 102011113611 B3 | 10/2012 |
| JP | 3203211 B2 | 3/1999 |

OTHER PUBLICATIONS

EP 22166624; filed Apr. 5, 2022; European Search Report dated Sep. 26, 2022 (45 pages).
Smit et al.; Relative Dosimetry in a 1.5 T Magnetic Field: An MR-Linac Compatible Prototype Scanning Water Phantom; Institute of Physics and Engineering in Medicine; Phys. Med. Biol 59 (2014) 4099-4109; Jul. 3, 2014 (11 pages).
DE 202110111815; filed May 6, 2021; German Office Action dated Oct. 5, 2023 (7 pages).

\* cited by examiner

*Primary Examiner* — David P Porta
*Assistant Examiner* — Casey Bryant
(74) *Attorney, Agent, or Firm* — Barclay Damon LLP (57) ABSTRACT

A method for validating the axis linearity of a displacement mechanism for a radiation detector configured to detect high-energy radiation emitted by an irradiation device comprises providing a container configured to receive a liquid. A tactile sensor and a standard element are positioned within the container configured for receiving the liquid. A displacement mechanism is structured to displace at least one of: (1) the tactile sensor; and (2) the standard element along at least one spatial axis. The tactile sensor is used to tactilely detect the standard element.

17 Claims, 5 Drawing Sheets

DEVICE FOR VALIDATING THE AXIS LINEARITY AND/OR THE POSITIONING ACCURACY OF A DISPLACEMENT MECHANISM FOR A RADIATION DETECTOR AND ASSOCIATED METHOD OF PRACTICE

CROSS REFERENCE TO RELATED INVENTION

This application is based upon and claims priority to, under relevant sections of 35 U.S.C. § 119, German Patent Application No. 10 2021 111 815.8, filed May 6, 2021, the entire contents of which are hereby incorporated by reference.

TECHNOLOGICAL FIELD

This disclosure relates to a method and a device for validating the axis linearity and/or the positioning accuracy of a displacement mechanism for a radiation detector, which is configured for detecting high-energy radiation emitted by an irradiation device.

BACKGROUND

In the field of medicine, irradiation devices are employed to treat malignant tissue. For example, highly accelerated particle radiation generated by means of a linear particle accelerator (LINAC) or respectively electromagnetic radiation is aimed at the tissue to be treated. Such a radiation treatment must be performed very precisely both with regard to the location of impact of the radiation and with regard to the intensity of the radiation on the location of impact in order to avoid damaging healthy tissue. To plan such treatments, computer systems are used which are reliant on data that is as exact as possible, in particular in relation to the location of impact and the intensity of the radiation at the location of impact, meaning at the location of the intended interaction between radiation and the tissue to be treated.

Therefore, before the irradiation, a measurement of the radiation generated by the radiation source is typically performed, in particular with regard to its intensity and also with regard to its location of impact. In doing so, the radiation measurement is usually performed using an irradiation target which has a density comparable to the human body. Thus, a container filled with water, also known as a water phantom, is typically used as an irradiation target, wherein a detector for detecting the radiation is arranged within the water phantom. In this case, the detector is usually arranged movably in all three spatial directions X, Y, Z within the water phantom in order to be able to measure the intensity of the radiation at various locations within the water phantom. To move the detector along the three spatial directions which are orthogonal to each other, a displacement mechanism is used which can comprise one or more carriages that can be shifted on rails, wherein the detector is arranged on one of the rails. Usually three carriages are provided in order to be able to shift the detector along the three spatial directions which are orthogonal to each other.

For the radiation detector to deliver informative data, it must be ensured in particular that the displacement mechanism displaces the detector in as exact a manner as possible in conformance with a specification. Thus, for example, a control unit can specify a movement of 10 mm along the x-axis and control the displacement mechanism accordingly to move the radiation detector. During the movement of the radiation detector and in particular of the carriage carrying it along the respective movement axis, however, undesired deviations can occur. Therefore, a regular verification of the actual axis position assumed by the displacement mechanism and with it the radiation detector and/or the axis linearity of the movement of the same is of significant importance.

Known systems for validating the axis linearity provide an interferometric measurement system arranged outside of the water phantom, comprising, for example, a measuring laser which is aimed at the radiation detector or respectively the carriage carrying it. Such systems, however, have multiple disadvantages. With such an external system, the axis linearity of the radiation detector cannot be established under real conditions. This is because, on the one hand, the water phantom can impair the measurement in its water-filled state. On the other hand, the mentioned radiation sources for treating malignant tissue are often employed in combination with a magnetic resonance tomograph (MRT) and thus in a strong magnetic field. Ideally, the water phantom is brought onto the patient couch on which the patient intended for the treatment should then lie later. Such a positioning of the water phantom within the MRT, however, prevents a measurement with such an external measurement system for reasons of space. In addition, the strong magnetic field impairs the external measurement system. Designing the parts of the external measurement system to be MR-suitable is complex and expensive.

Starting from this prior art, the object of the invention is to provide a method as well as a device for validating the axis linearity of a radiation detector which enable a particularly reliable validation, in particular also within a strong external magnetic field and under water.

BRIEF SUMMARY OF THE INVENTION

An embodiment of a method for validating the axis linearity and/or the positioning accuracy of a radiation detector includes displacing a tactile sensor element arranged within a container for receiving a liquid along at least one spatial axis via a displacement mechanism to tactilely detect a standard element arranged within the container. Alternatively or additionally, the method can include displacing a standard element arranged within the container for receiving a liquid along at least one spatial axis via a displacement mechanism to tactilely detect the standard element by means of the tactile sensor element.

An embodiment of a device for validating the axis linearity and/or the positioning accuracy of a radiation detector comprises a container for receiving a liquid, the displacement mechanism, and a tactile sensor element arranged within the container. The sensor element is configured for tactilely detecting a standard element arranged within the container. The sensor element and/or the standard element can be displaced relative to each other along at least one spatial axis via the displacement mechanism. The sensor element can thus be brought in contact with the standard element.

In an embodiment of the method according to the invention and in an embodiment of the device according to the invention, the sensor element and standard element can thus be moved relative to each other. The sensor element can be movable via the displacement mechanism and the standard element can be spatially fixed, in particular spatially fixed in relation to the container. Also, the standard element can be movable via the displacement mechanism and the sensor element can be spatially fixed, in particular spatially fixed in relation to the container. In principle, both the sensor element and the standard element can also be movable, at least one of the two via the displacement mechanism.

The disclosed embodiments of the device are suitable for executing the disclosed method for validating the axis linearity and/or the positioning accuracy of a radiation detector. In particular, the device can comprise a control unit that serves to perform the method according to the invention. The method and the device are explained together in the following. Explanations made for the method also apply accordingly for the device and vice versa.

An embodiment of the device for validating the axis linearity and/or the positioning accuracy of a radiation detector comprises a container for receiving a liquid, in particular for receiving water, as well as a displacement mechanism. The container including the displacement mechanism is also referred to below as a water phantom, wherein instead of water, however, another liquid can also be used in principle. The device also comprises a tactile sensor element which can be displaced along at least one spatial axis, preferably, however, along two or three spatial axes which are orthogonal to each other, via a displacement mechanism. Alternatively, the standard element can also be displaceable accordingly, as explained above. For reasons of simplicity, in the following, displacing or moving the sensor element by means of the displacement mechanism will usually be spoken of, wherein it is clear to the person skilled in the art that displacing or moving the standard element relative to the sensor element is alternatively also meant. The displacement mechanism can have one or more carriages for this which can be moved relative to each other. The sensor element or respectively the standard element is thereby arranged within the container movably relative to the container via the displacement mechanism. The displacement mechanism itself, in particular its carriages, are also preferably arranged within the container.

An embodiment of the device according to the invention with its water phantom serves in the manner explained above for initial setup or respectively quality assurance of linear accelerators, in particular of what are known as magnetic resonance linear accelerators (MR-LINACs). The axis positioning accuracy of water phantoms must also be proven in MR-LINAC irradiation rooms in the magnetic field as part of commissioning. MR-LINACs combine the irradiation unit, meaning the linear accelerator, and the MRT into one device, as already discussed above. Thus the irradiation object, for example a tumor, and the adjacent healthy normal tissue can be made visible by means of MR and the treatment beam can then be exactly aimed at the tumor. Surrounding tissue can thus be protected. For example, the tactile sensor element can be arranged on the displacement mechanism instead of the radiation detector, as will be explained later. The displacement mechanism of the tactile sensor element is in particular the same one that carries and displaces the radiation detector in the usual use of the water phantom. The displacement mechanism can have, for example, an adapter or receiving element which carries the tactile sensor element.

By means of the tactile sensor element or respectively standard element displaceable via the displacement mechanism, the axis linearity and the positioning accuracy of the displacement mechanism of the radiation detector, and thus the axis linearity and the positioning accuracy of the radiation detector itself, can be validated. Validating the positioning accuracy means here in particular verifying whether a specified position in space is also reached exactly. Validating the axis linearity means in particular verifying whether the requested movement is implemented in the desired manner, meaning whether, for example, a movement of the radiation detector or respectively of the part of the displacement mechanism carrying it is carried out between two points according to a specified distance in the manner indicated already earlier. In particular, a position determination can be performed at multiple positions along a movement axis of the sensor element or respectively of the displacement mechanism. In this way, one or more axis positions can be validated. The validation of the axis linearity can be carried out on this basis. A control unit can be provided to control the displacement mechanism for moving the sensor element. This can be configured to verify and, if applicable, readjust a movement of the displacement mechanism and thus of the sensor element as well as in particular the conformity of this movement. A calibration of the displacement mechanism can thus also be provided.

The invention is distinguished from the prior art in that, on the one hand, a tactile sensor element is provided, meaning a position determination is carried out tactilely, as well as, on the other hand, in that this tactile sensor element is arranged within the water phantom. By means of the tactile sensor element, a standard element, also arranged within the water phantom, can be tactilely detected. The sensor element can comprise, for example, a sensor head which is brought in contact with the standard element to tactilely detect the standard element. A standard element is to be understood as an element, the measurement or detection of which by the sensor element allows a conclusion to be drawn about the position of the displacement mechanism and/or about a distance traveled by the displacement mechanism. A standard element is to be understood in particular as an element with defined dimensions. In this case, it does not need to be a standard element based on a standard such as, for example, a DIN standard. In particular, the standard element can be regarded as a material measure. By means of the invention, a validation of the axis position or respectively the axis linearity of the sensor element or respectively the displacement mechanism can thus be carried out. In contrast to the prior art, no external measurement system is thus provided, such as, for example, a laser aimed at the radiation detector in the water phantom. Instead, the system provided for the validation is arranged, in particular integrated, within the water phantom. In other words, the invention is based on the idea of using the water phantom, including its container and its displacement mechanism, for the validation by detecting a standard element within the container via the tactile sensor element.

Thus, work can be done under real conditions, namely, in particular, within the water-filled container, on the one hand, as well as within the external magnetic field generated by the MRT. The entire device can be brought onto the patient couch of the MR-LINAC for the validation and can perform the validation under real conditions, meaning in particular with an active magnetic field of the MRT and, if applicable, also with the phantom filled with water. Since there is a tactile sensor element according to the invention, the external magnetic field does not disrupt the validation. The tactile detection of the standard element arranged within the container by the tactile sensor element is also possible with a strong external magnetic field without a notable impairment of the measurement accuracy. The method according to the invention or respectively the device according to the invention thus allow a reliable validation of the respectively controlled axis position and the axis linearity of the displacement mechanism and thus of the radiation detector under real conditions. The components of the system according to the invention, in particular the tactile sensor element and the standard element, can be configured in a cost-effective manner to be MR-suitable, meaning resistant to the external magnetic field of the MRT. Mechanical parts such as the standard elements can thus consist, for example, of ceramic or aluminum. A sensor head of the sensor element can in particular comprise non-ferromagnetic metal or be configured as a simple electrical part, in particular as a contact switch. After performing this validation, it can be verified by the radiation detector in a manner known per se whether the treatment beam of the linear accelerator impinges on the desired location with the desired intensity.

According to one embodiment, the tactile sensor element is configured to be displaceable along two or three spatial axes which are orthogonal to each other to tactilely detect the standard element. The method for validating the axis linearity and/or the positioning accuracy of a radiation detector can correspondingly comprise the step displacing the tactile sensor element along two or three spatial axes which are orthogonal to each other to tactilely detect the standard element. The displacement mechanism can be configured accordingly. The displacement mechanism can thus comprise, for example, two or three carriages movable relative to each other which enable the movement of the sensor element carried on the displacement mechanism along the two or three spatial axes which are orthogonal to each other. The displacement along the axes which are orthogonal to each other means in this case a displacement such that the sensor element is moved from a first position $X_1, Y_1, Z_1$ to a second position $X_2, Y_2, Z_2$. This can be carried out in three movement steps that are perpendicular to each other along the respective axes or also in a joint movement, for example along a diagonal. This can also be achieved, in spherical coordinates, by moving along an axis and changing two angles.

According to one embodiment, the standard element is configured as a test plate with surface features such as indentations and/or protrusions, wherein the sensor element is driven along the indentations and/or protrusions to tactilely detect the test plate. In principle, the test plate can also be shiftable by means of the displacement mechanism, meaning moved along the sensor element such that its sensor head recognizes the indentations and/or protrusions. The test plate can be arranged within the water phantom such that the tactile sensor element can be shifted along the test plate. The test plate can have, for example, indentations in the form of grooves. A sensor head of the sensor element can be shifted, for example, into such an indentation and then be moved along a longitudinal extent of the indentation. The sensor head can consist, as a probe head in particular, of a non-ferromagnetic metal. For example, circular indentations or respectively protrusions, for example annular grooves, can be provided or also rectangular. The sensor element can thus be shifted along the indentations or respectively protrusions of the test plate in particular at least along two spatial axes which are orthogonal to each other. For example, the test plate can be arranged in the X-Z plane so that the tactile sensor element can be shifted along the indentations or respectively protrusions also arranged in this plane. Thus, at least in relation to the X and Y-axes, the axis position or respectively axis linearity of the displacement mechanism and thus of the radiation detector can be validated. The test plate can also be positioned in a different manner within the container, for example in a subsequent method step, and be traversed again by the sensor element. The test plate, for example, can thus be oriented along the Y-Z plane. Traversing the indentations or respectively protrusions of the test plate by the sensor element then also allows a validation of the axis position or respectively axis linearity along the Y-axis.

According to one embodiment, the standard element comprises at least one gauge block, wherein the sensor element is displaced into contact with the gauge block to tactilely detect the gauge block. In principle, the gauge block can also be displaceable, meaning the gauge block can be driven up to the sensor element. The sensor head of the sensor element can in this case be configured as a simple electrical part, in particular as a contact switch. The tactile sensor element can be displaced along one of the three spatial axes in particular via the displacement mechanism, meaning from a starting position at a distance from the gauge block toward an end position in contact with the gauge block. As a standard element, the gauge block has an exactly defined length, as mentioned, which enables a validation of the axis position or respectively axis linearity, in particular when multiple gauge blocks are tactilely detected in such a way in multiple steps. The gauge blocks can consist, for example, of ceramic.

According to one embodiment, it is thus provided that the standard element comprises multiple gauge blocks which are tactilely detected by the sensor element one after another in multiple steps or sequential steps. The gauge blocks can also be moved instead. The gauge blocks can have the same or different lengths. The gauge blocks can be received, for example, in a gauge block guide which is oriented along one of the three spatial axes. To validate the axis position or respectively axis linearity, first, for example, a first gauge block of a first length can be placed and detected by the sensor element, meaning driven up to by the sensor element. Then, the first gauge block can be replaced by a second gauge block of a larger, second length, wherein the second gauge block is in turn detected, meaning driven up to, by the sensor element. The second gauge block can also be placed against the first gauge block and then detected. The sensor element thus traverses differently long paths in sequential steps. In this case, the sensor element can comprise, for example, a contact switch as a sensor head, which triggers upon contact with the respective gauge block. As part of the validation of the axis position or respectively axis linearity, the trigger position at which the sensor element triggers due to the tactile detection of the respective gauge block, is then established in each case. The trigger position can be detected automatically by the control unit, or can also in principle be manually noted. Using the standardized gauge blocks, the validation can thus be carried out in a simple manner and also within the external magnetic field and within the water phantom. The method will be explained in detail later.

According to a related embodiment, some of the steps take place outside and some of the steps take place within the magnetic field of a magnetic resonance tomograph (MRT). In particular, all steps can also take place within the magnetic field. For example, a first gauge block can be driven up to when the device is arranged outside of the external magnetic field and a second gauge block can be driven up when the device is arranged within the external magnetic field of the MRT. The device can be arranged for this, for example, on a movable patient couch of the MRT or respectively MR-LINAC, wherein this is driven once into the magnetic field and once out of the magnetic field. This can improve the validation even more, as will become clear in the detailed explanation to follow later.

According to one embodiment, the tactile sensor element is arranged at the point on the displacement mechanism provided for the radiation detector. In particular, the tactile sensor element can be arranged on the already mentioned receiving element, which otherwise carries the radiation detector. The receiving element can thus be configured for selectively receiving the radiation detector and the sensor element. By positioning the tactile sensor element at the point on the displacement mechanism provided for the radiation detector, a particularly secure validation can be achieved.

According to one embodiment, the device comprises a control unit for performing the method, as already discussed. The method can thus be executed partially, preferably completely, automatically. In particular, the sensor element or respectively the standard element can be displaced automatically via the control unit, meaning the displacement mechanism can be controlled accordingly. Thus, for example, with a test plate as a standard element, the sensor element can be moved automatically along the indentations or respectively protrusions via the control unit. In one embodiment of the standard elements as gauge blocks, they can also be automatically driven up to by the sensor element. The method according to the invention can thus be at least partially automated.

BRIEF DESCRIPTION OF THE DRAWINGS

Embodiments of the invention are explained below using figures. In the drawings.

If not otherwise specified, the same reference numbers indicate the same objects below.

DETAILED DESCRIPTION OF THE INVENTION

Figure 1:
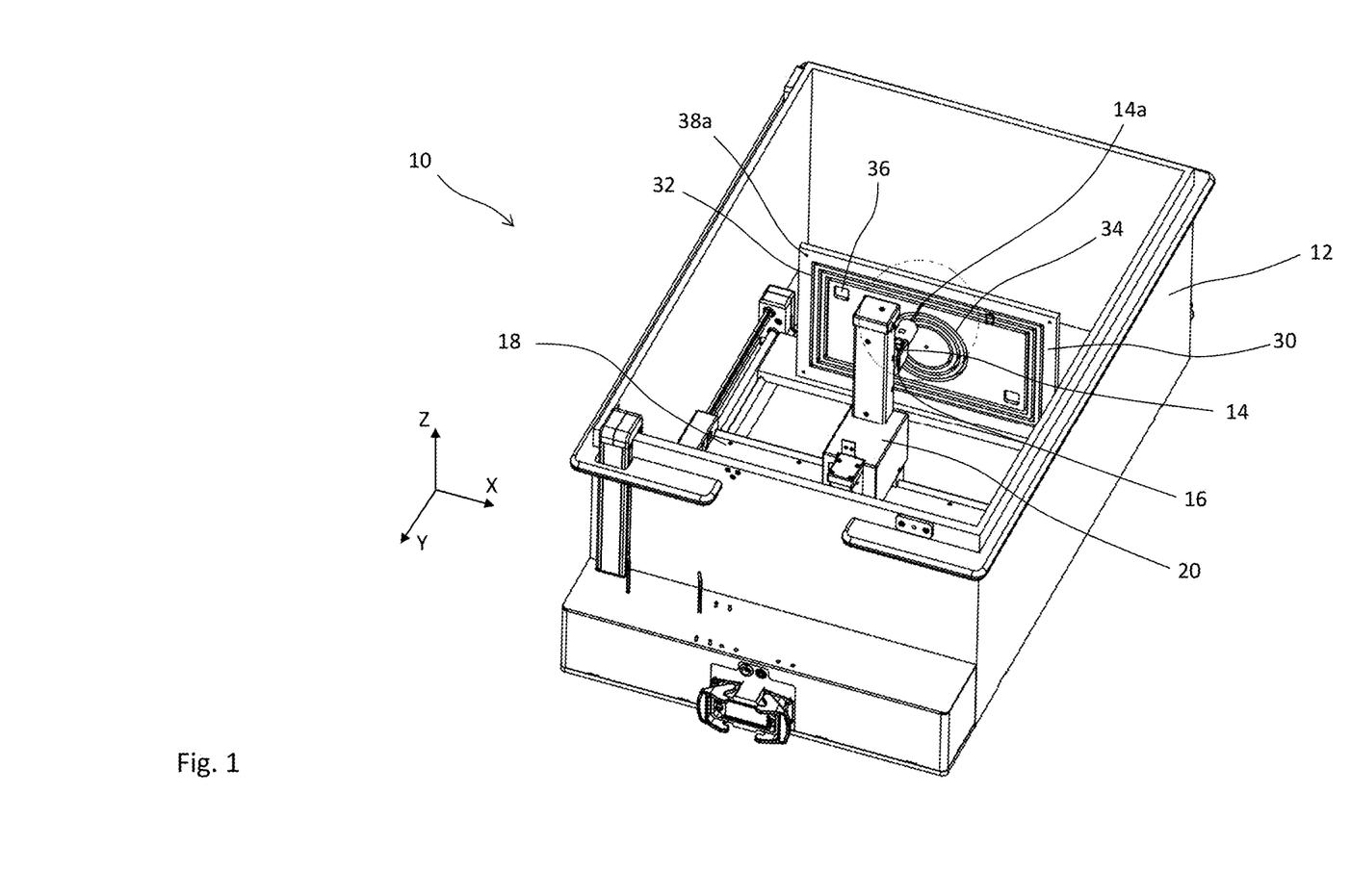
FIG. 1 illustrates a perspective view of an embodiment of a device for validating the axis linearity and/or the positioning accuracy of a radiation detector.

In FIG. 1, a first embodiment of the device according to the invention can be seen. The device 10 shows a water phantom comprising a container 12 which can be filled with water. A tactile sensor element 14 with a sensor head 14a is arranged within the container 12. The sensor element 14 can be displaced via a displacement mechanism 16, 18, 20 which comprises three carriages with which the sensor element 14 can be displaced along the three spatial axes X, Y, and Z which are orthogonal to each other. The sensor element 14 is thus displaceable along the Z-axis via a first carriage 16, along the Y-axis via a second carriage 18, and along the X-axis via a third carriage 20. The first carriage 16 runs on a first rail 16a, the second carriage 18 runs on a second rail 18a, and the third carriage 20 runs on a third rail 20a (see FIG. 3). The rails 16a, 18a, 20a all run orthogonally to one another, each along one of the three spatial directions. The three carriages 16, 18, 20 and the rails 16a, 18a, 20a of the displacement mechanism are also arranged within the container 12 and can be understood as part of the water phantom.

A standard element, configured in this embodiment as a test plate 30, is also located within the container 12. The test plate 30 has a rectangular shape and has multiple indentations configured therein, namely in form of rectangular running grooves 32 which extend along edge regions of the test plate 30, annular grooves 34 arranged centrally in the test plate 30, and rectangular indentations 36 arranged in opposing corner regions of the test plate. Bores 38a are also configured in the corners of the test plate 30 and a central bore 38b in the middle.

The water phantom serves generally to check whether high-energy radiation emitted by an external irradiation device arrives at a desired position at a desired intensity. The irradiation device is in particular a linear accelerator which is preferably used in combination with an MRT. By means of such MR-LINACs, an object to be irradiated, such as, for example, a tumor, can be concretely identified via the MRT and then exactly focused by means of the treatment beam emitted by the linear accelerator. It is checked, with a water phantom comprising a radiation detector, at regular intervals and in particular for planning the treatment whether the treatment beam also actually impinges at the desired position at the desired intensity. For this purpose, the water phantom can have a radiation detector on the displacement mechanism 16, 18, 20. For an informative verification, it is of significant importance that the displacement mechanism shifts the radiation detector in exactly the specified manner. For this purpose, the axis position or respectively axis linearity of the radiation detector must be validated.

Figure 2A:
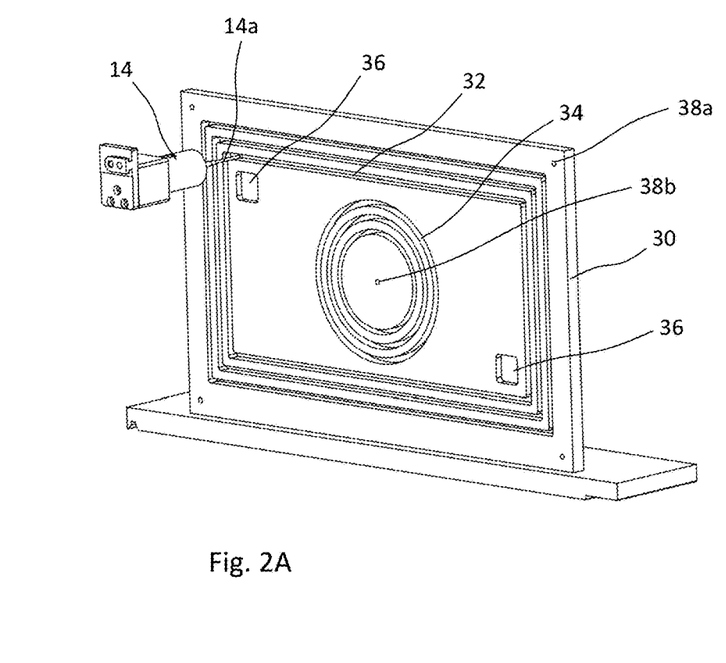
FIG. 2A illustrates a perspective view of an embodiment of a standard element configured as a test plate.
Figure 2B:
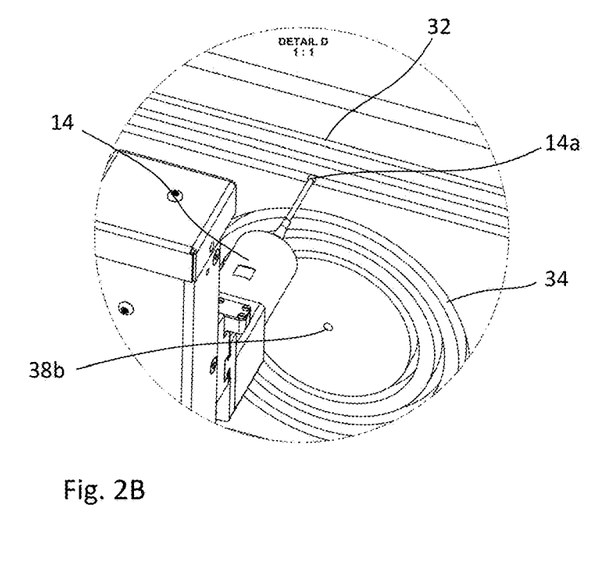
FIG. 2B illustrates a close-up view of a portion of the embodiment of FIG. 2A.

The device according to the invention enables such a validation. For this purpose, in the embodiment according to FIGS. 1 and 2, the sensor element 14 is arranged at the point of the displacement mechanism otherwise provided for the radiation detector. Thus, the carriage 16 can have a receiving element (not shown) which usually carries the radiation detector, but in the present case has the sensor element 14 instead of the radiation detector. By traversing the test plate 30 by means of the sensor element 14, the axis position or respectively axis linearity of the displacement mechanism and thus also of the radiation detector can be validated. In particular, it can be verified whether the displacement mechanism implements a desired movement requirement in exactly the desired manner. If not, it can be readjusted or respectively calibrated.

In the embodiment from FIGS. 1 and 2, the tactile sensor element 14 drives with its sensor head 14a along the grooves 32, 34 for this purpose. To initially align the sensor element 14 with the test plate 30, the rectangular indentations 36 can be driven up to previously as a starting point. The dimensions of the sensor head 14a and the grooves 32, 34 are thereby coordinated with each other such that a specified tolerance of the axis linearity is complied with. Spot checks at the bores 38a arranged in the corners of the test plate 30 and at a central bore 38b can also be done. The sensor head 14a and the test plate 30 can be configured to be electrically conductive so that touching of the test plate 30 by the sensor head 14a can be ascertained by corresponding sensors. In particular, a water-tight probe head can be provided as the sensor head so that the performance of the method is possible even with the container filled with water. The sensor element can now be shifted along the grooves 32, 34 via a control unit and thus the axis position or respectively axis linearity of the displacement mechanism in the X-Z plane can be validated.

In FIGS. 2a and 2b, it can be seen in detail how the sensor head 14a is moved along one of the indentations 32. As can be seen, the sensor head 14a enters the indentation 32 for this purpose. To also validate the axis position or respectively axis linearity along the Y-axis, another such measurement of the test plate can be provided, wherein the test plate is then oriented, for example, along the Y-Z plane and can be traversed by a correspondingly arranged sensor element. In principle, a validation along the Y-axis can also be carried out in that, in the arrangement of the test plate 30 in the X-Z plane that can be seen in FIG. 1, the sensor head is shifted into and again out of one or more of the indentations 32 to 36 along the Y-axis.

The device according to the invention can be arranged at a point on a patient couch provided for the water phantom within the magnetic field of the MRT and the method according to the invention can be performed there. The tactile detection of the test plate 30 by the tactile sensor element 14 is not impaired by the external magnetic field, very much in contrast to the previously known measurement methods, in which a laser arranged outside of the water phantom is aimed at the displacement mechanism. The components of the device according to the invention, in particular the sensor head 14a and the test plate 30, can be configured to be MR-suitable in a simple manner by selecting the material accordingly. The arrangement of the sensor element within the water phantom is also space-saving and enables the method according to the invention to be performed in particular in the actual, later use position of the water phantom, namely on the patient couch within the MRT.

With the device according to FIGS. 1 and 2, the axis position or respectively axis linearity of the radiation detector can thus be validated along all three spatial axes in a particularly simple and reliable manner under real conditions. The same applies to the second embodiment explained in the following.

FIGS. 3 to 6 show another embodiment of a device according to the invention which differs from the one previously explained in that, instead of the test plate 30, precision gauge blocks 42, 44, 46 are provided as standard elements, which can consist in particular of ceramic and can thus be MR-suitable.

Figure 3:
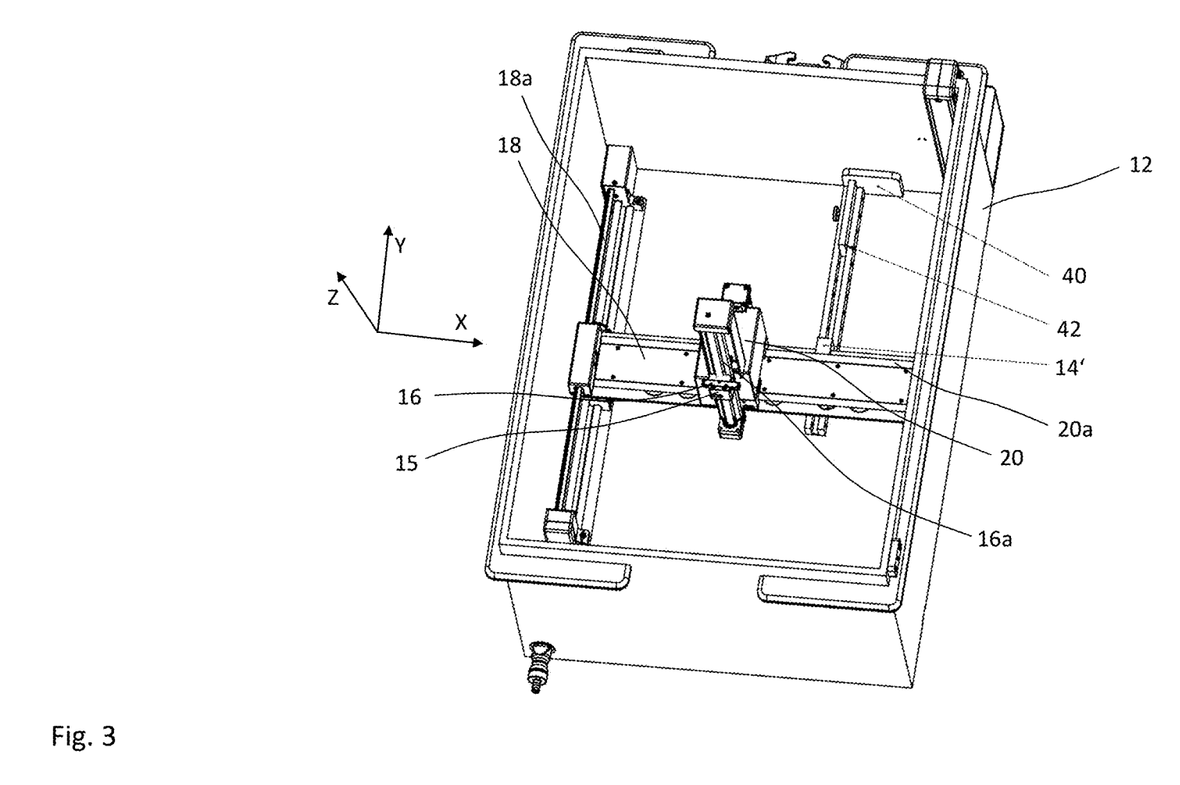
FIG. 3 illustrates a perspective view of another embodiment of the device for validating the axis linearity and/or the positioning accuracy of a radiation detector including gauge blocks as standard elements for validating the axis position or respectively axis linearity along the Y-axis.

FIG. 3 shows a tactile sensor element 14' which is arranged on the second carriage 18 and is thus movable along the Y-axis. A gauge block guide 40 which receives a gauge block 42 in FIG. 3 extends along the Y-axis. In this view, the receiving element 15 already discussed previously can be seen on the first rail 16, which element serves to receive the radiation detector. In this embodiment, however, the sensor element 14' is not arranged on this receiving element, as can be seen.

The sensor element 14' has a sensor head 14a' configured as a contact switch which triggers upon contact with one of the gauge blocks 42, 44, 46. To tactilely detect the gauge blocks, the sensor element 14' is displaced along the Y-axis toward the gauge block 42 visible in FIG. 3, wherein, when the contact switch 14a', visible in FIG. 4, of the sensor element 14' is impinged upon, the contact switch 14a' triggers. This is explained in the following using FIG. 4.

Figure 4A:
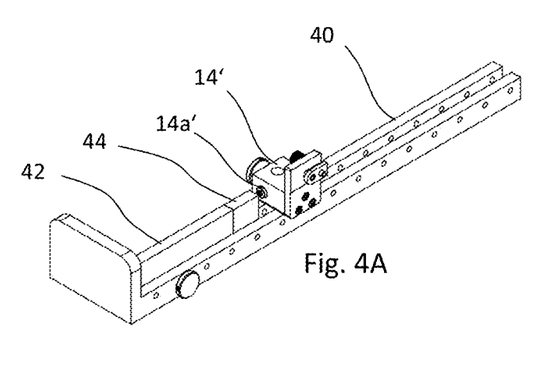
FIG. 4A illustrates a perspective view of an embodiment of the device for validating the axis linearity and/or the positioning accuracy of a radiation detector including multiple gauge blocks used as standard elements.
Figure 4B:
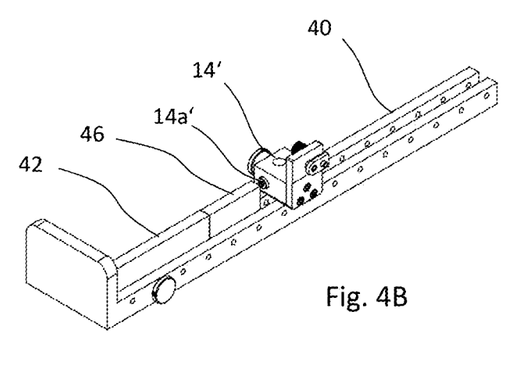
FIG. 4B illustrates a perspective view of another embodiment of the device for validating the axis linearity and/or the positioning accuracy of a radiation detector including multiple gauge blocks used as standard elements.
Figure 4C:
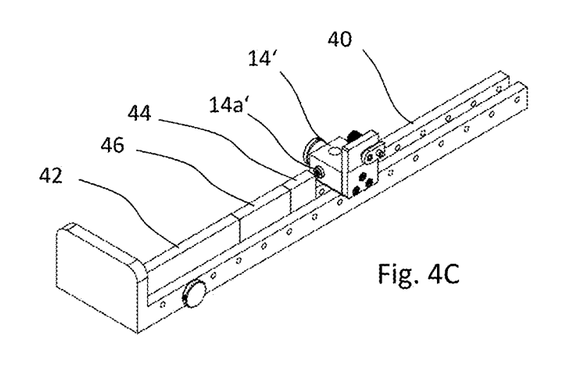
FIG. 4C illustrates a perspective view of another embodiment of the device for validating the axis linearity and/or the positioning accuracy of a radiation detector including multiple gauge blocks used as standard elements.

In FIGS. 4a-c, multiple different gauge blocks 42, 44, 46 are received in the gauge block guide 40. As can be seen, a first gauge block 42 has a first length and a second gauge block 44 has a second length, wherein the second length is shorter than the first length. In addition, a third gauge block 46 has a third length which lies between the first and the second length. In the context of the method according to the invention, multiple of these gauge blocks 42, 44, 46 are now tactilely detected by the sensor element 14', meaning driven up to by the sensor element 14', one after another in multiple steps such that the contact switch 14a' triggers. Thus, according to FIG. 4a, the gauge blocks 42, 44 are first placed into the gauge block guide 40 and driven up to by the sensor element 14'. The result is a first trigger position which can be detected, for example, by a control unit of the device. Then the sensor element 14' is shifted away from the gauge blocks 42, 44 again and the gauge block 44 is replaced by the gauge block 46, as can be taken from FIG. 4b. Following this, the sensor element 14' is driven up to the gauge block 46 so that the contact switch 14a' in turn triggers and the trigger position is once again recorded. Finally, the sensor element 14' is driven away from the gauge block 46 again and the gauge block 44 is additionally inserted, as can be taken from FIG. 4c. The sensor element 14' is in turn driven to the gauge blocks so that the contact switch 14a' comes in contact with the gauge block 44. The trigger position is in turn recorded. This procedure can be repeated for additional gauge block lengths. The gauge blocks can of course also be placed and driven up to in a different sequence. The key is that the gauge blocks form a different length overall in each method step.

In a concrete embodiment, for example, first the sensor element 14' can be shifted towards the gauge blocks in 0.1 mm steps until the contact switch 14a' triggers. Then the trigger position is noted. Then the sensor element 14' is driven away from the gauge blocks by 0.5 mm. In a next step, the patient couch carrying the water phantom 12 and with it the entire device can be shifted into the magnetic field of the MRT. Following this, the sensor element 14' is driven up once again to the same gauge blocks step by step in 0.1 mm steps until the contact switch triggers. Once again the trigger position is noted. Then the sensor element 14' is in turn driven away from the gauge blocks by 10 mm, then in turn shifted toward the gauge blocks by 9.5 mm. Then the sensor element 14' is driven up to the gauge blocks in 0.1 mm steps until the contact switch triggers. The trigger position is in turn noted. In another step, the sensor element 14' is driven away from the gauge blocks by 12 mm and the patient couch is then shifted out of the magnetic field. Then the gauge block is extended by 10 mm, meaning a corresponding gauge block can be placed or respectively the previous gauge block can be replaced by a gauge block of the corresponding length. Following this, the sensor element 14' is once again shifted in the direction of the gauge block. These steps are then repeated for three to four different gauge block lengths.

In this manner, multiple positions along the Y-axis are validated in the present exemplary embodiment, from which the axis linearity can in turn be validated. Performance within as well as outside of the magnetic field can lead to particularly informative results by comparing the measurements within the magnetic field to those outside of the magnetic field. For repeated quality assurance, first only one measurement can also be performed within the MR and, in the event of any deviation, a measurement can also be performed outside of the MR to isolate the errors. The performance within and outside of the magnetic field can also confirm the independence of the method according to the invention from the magnetic field, if required.

Figure 5:
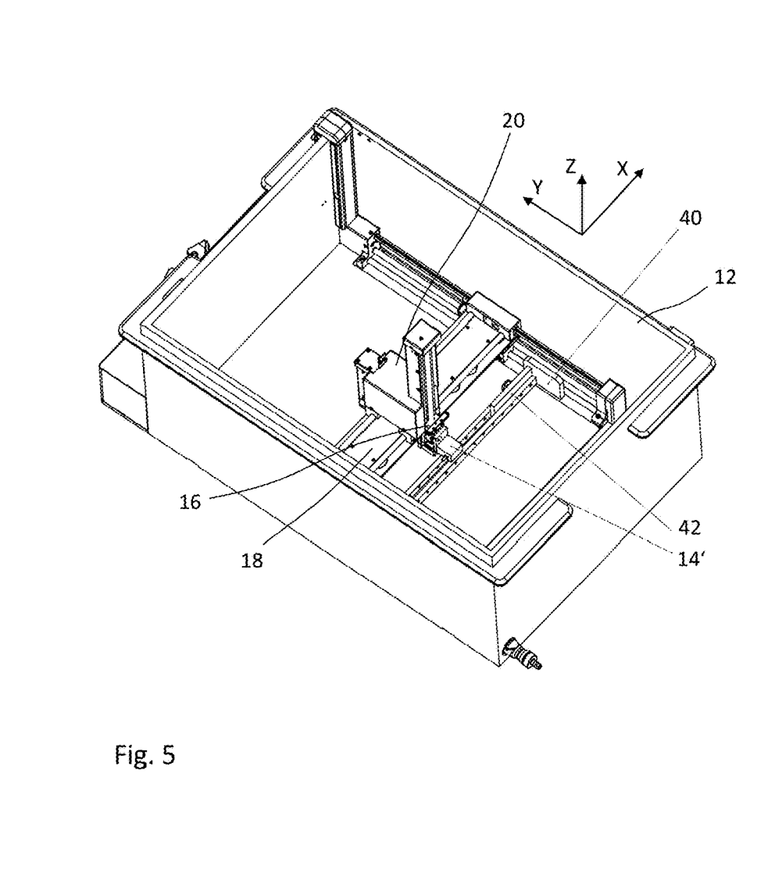
FIG. 5 illustrate a perspective view of an embodiment of a device for validating the axis linearity of a radiation detector with gauge blocks as standard elements for validating the axis position or respectively axis linearity along the X-axis.
Figure 6:
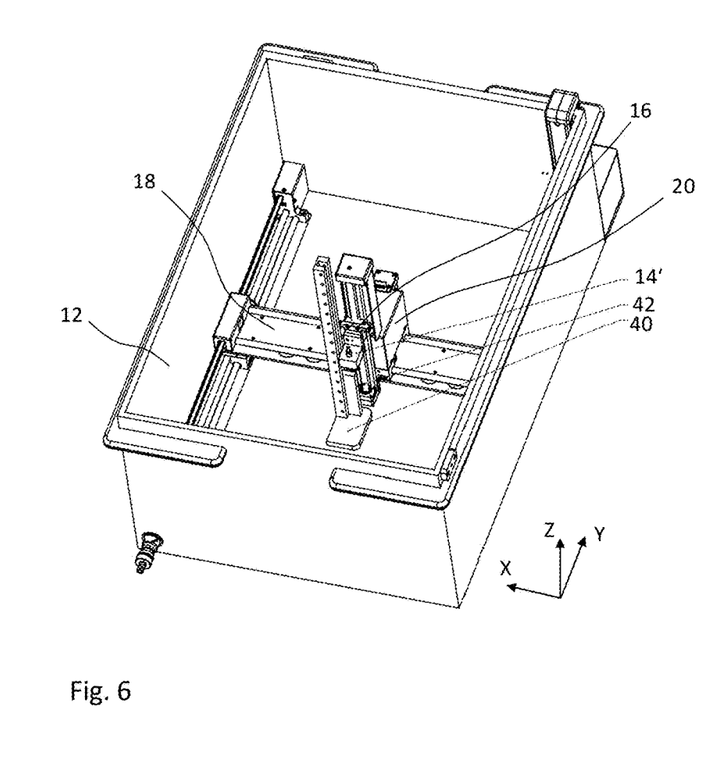
FIG. 6 illustrates a perspective view of an embodiment of a device for validating the axis linearity and/or the positioning accuracy of a radiation detector with gauge blocks as standard elements for validating the axis position or respectively axis linearity along the Z-axis.

To also validate the axis position or respectively axis linearity along the X-axis and the Z-axis, the gauge block guide 40 with its gauge blocks can be arranged accordingly along the respective axes, as can be taken from FIGS. 5 and 6. In FIG. 5, the gauge block guide 40 is arranged running along the X-axis. The sensor element 14' is arranged on the receiving element 15 on the carriage 16 for this and is oriented such that the contact switch contacts the gauge block 42 with a movement along the X-axis.

In FIG. 6, the gauge block guide 40 runs along the Z-axis. Accordingly, the sensor element 14' arranged on the receiving element 15 on the carriage 16 here as well is oriented with its contact switch such that the contact switch contacts the gauge block 42 with a movement along the Z-axis. In a comparable manner—as explained previously—the axis position or respectively axis linearity can also thus be validated along the X and Z-axis.

In a simple manner, the parts of the device according to the invention can be configured to be MR-suitable. Mechanical parts can thus consist of ceramic or respectively aluminum, the sensor head can consist of non-ferromagnetic metal or respectively as a simple electrical contact switch. Thus, the entire device, as already discussed, can be used within the magnetic field. The method according to the invention can also be performed with the phantom filled with water.

The invention claimed is:

1. A method for validating an axis linearity of a displacement mechanism for a radiation detector configured to detect high-energy radiation emitted by an irradiation device, the method comprising:
   providing a container configured to receive a liquid;
   positioning a tactile sensor and a standard element within the container configured for receiving the liquid;
   structuring a displacement mechanism to displace at least one of: (1) the tactile sensor; and (2) the standard element along at least one spatial axis; and
   tactilely detect the standard element using the tactile sensor element.

2. The method according to claim 1, comprising displacing the at least one of: (1) the tactile sensor; and (2) the standard element, along at least two spatial axes that are orthogonal to each other in order to tactilely detect the standard element using the tactile sensor.

3. The method according to claim 1, further comprising,
   configuring the standard element as a test plate defining a plurality of surface features, and
   driving the tactile sensor along the plurality of surface features to tactilely detect the test plate.

4. The method according to claim 1, further comprising,
   configuring the standard element as a test plate defining a plurality of surface features, and
   driving the test plate along the tactile sensor via the plurality of surface features.

5. The method according to claim 1, wherein the standard element comprises at least one gauge block, and further comprising driving the tactile sensor in contact with the at least one gauge block to tactilely detect the at least one gauge.

6. The method according to claim 1, wherein the standard element comprises at least one gauge block, and further comprising driving the at least one gauge block in contact with the tactile sensor to tactilely detect the at least one gauge block.

7. The method according to claim 5, wherein the standard element comprises multiple gauge blocks, and further comprising tactilely detecting each of the multiple gauge blocks in sequential steps.

8. The method according to claim 7, wherein at least one of the sequential steps is carried out within a magnetic field of a magnetic resonance tomograph (MRT).

9. A device for validating positioning accuracy of a displacement mechanism for a radiation detector for detecting high-energy radiation emitted by an irradiation device, the device comprising:
   a container configured to receive a liquid;
   the displacement mechanism; and
   a sensor element arranged within the container, wherein the sensor element is configured to tactilely detect a standard element arranged within the container, and wherein the displacement mechanism is configured to displace at least one of: (1) the sensor element; and (2) the standard element relative to another of the sensor element and the standard element along at least one spatial axis.

10. The device according to claim 9, wherein the at least one of the sensor element and the standard element are displaced along at least two spatial axes that are orthogonal to each other.

11. The device according to claim 9, wherein the standard element is a test plate defining a plurality of surface features, and wherein the sensor element is configured to be driven along the plurality of surface features to tactilely detect the test plate.

12. The device according to claim 9, wherein the standard element is a test plate defining a plurality of surface features, and wherein the test plate is configured to be driven along the plurality of surface features of the sensor element.

13. The device according to claim 9, wherein the standard element comprises at least one gauge block, and wherein the sensor element is configured to be driven in contact with the gauge block to tactilely detect the gauge block.

14. The device according to claim 9, wherein the standard element comprises at least one gauge block, and wherein the gauge block is configured to be driven in contact with the sensor element to tactilely detect the gauge block.

15. The device according to claim 13, wherein the standard element comprises multiple gauge blocks, and wherein the sensor element is configured to be driven in contact with each of the multiple gauge blocks in a sequential manner to tactilely detect each respective gauge block.

16. The device according to claim 9, wherein the sensor element is arranged at a location on the displacement mechanism comprising a radiation detector.

17. The device according to claim 9, further comprising a control unit configured to control the displacement mechanism.

* * * * *